(12) United States Patent  
Luostarinen (10) Patent No.: US 9,560,721 B2
(45) Date of Patent: Jan. 31, 2017

(54) METHOD FOR CONTROLLING LIGHTING WITH A PORTABLE POINTER DEVICE

(71) Applicant: MERIVAARA OY, Lahti (FI)

(72) Inventor: Markku Luostarinen, Lahti (FI)

(73) Assignee: MERIVAARA OY, Lahti (FI)

( * ) Notice: Subject to any disclaimer, the term of this patent is extended or adjusted under 35 U.S.C. 154(b) by 0 days.

(21) Appl. No.: 14/764,261

(22) PCT Filed: Jan. 28, 2014

(86) PCT No.: PCT/FI2014/050065
§ 371 (c)(1),
(2) Date: Jul. 29, 2015

(87) PCT Pub. No.: WO2014/118432
PCT Pub. Date: Aug. 7, 2014

(65) Prior Publication Data
US 2015/0366036 A1    Dec. 17, 2015

(30) Foreign Application Priority Data
Jan. 30, 2013    (FI) ..................................... 20135088

(51) Int. Cl.
*H05B 37/02* (2006.01)
*G06F 3/0346* (2013.01)
*G06F 3/038* (2013.01)

(52) U.S. Cl.
CPC ........... *H05B 37/0227* (2013.01); *A61B 90/30* (2016.02); *G06F 3/0346* (2013.01); *G06F 3/0383* (2013.01);
(Continued)

(58) Field of Classification Search
CPC ... H05B 37/02; H05B 37/029; H05B 33/0815; H05B 37/083; Y02B 20/202; Y02B 20/14; F21W 2131/205; F21W 2131/406; G08C 19/28
(Continued)

(56) References Cited

U.S. PATENT DOCUMENTS 4,639,838 A    1/1987    Kato et al.
6,803,727 B2   10/2004   Laerum et al.
(Continued)

FOREIGN PATENT DOCUMENTS

EP    2 391 189 A2    11/2011
EP    2 413 018 A1    2/2012
(Continued)

OTHER PUBLICATIONS

International Search Report, dated Apr. 22, 2014, from corresponding PCT application.
(Continued)

*Primary Examiner* — Haissa Philogene
(74) *Attorney, Agent, or Firm* — Young & Thompson (57) ABSTRACT

A method (100) for controlling lighting includes using a portable pointer device, intended for the focusing of lighting, to determine (310) its position for establishing position data, and transmitting (150) the position data to a control unit, which is intended for controlling a lighthead and which controls the lighthead in such a way that the lighthead produces lighting for an object from a direction determined by the position data and location data, the location data having been established by determining a location of the pointer device in relation to the lighthead.

15 Claims, 3 Drawing Sheets

(52) U.S. Cl.
CPC ... *H05B 37/0272* (2013.01); *A61B 2034/2048* (2016.02)

(58) Field of Classification Search
USPC .. 315/129, 158, 294, 307, 308, 312; 362/33, 362/233; 340/12.22, 12.23
See application file for complete search history.

(56) References Cited

U.S. PATENT DOCUMENTS

| | | | | |
|---|---|---|---|---|
| 8,902,049 | B2* | 12/2014 | Fushimi | H05B 37/0272 340/12.22 |
| 8,981,913 | B2* | 3/2015 | Henig | H05B 37/0218 315/152 |
| 9,035,555 | B2* | 5/2015 | Fornasiero | A61B 19/5202 315/129 |
| 2008/0186720 | A1 | 8/2008 | Verbrugh | |
| 2010/0238282 | A1 | 9/2010 | Cinqualbre et al. | |
| 2011/0285515 | A1 | 11/2011 | Fushimi et al. | |
| 2012/0161647 | A1 | 6/2012 | Fornasiero et al. | |
| 2015/0035440 | A1* | 2/2015 | Spero | B60Q 1/04 315/153 |
| 2015/0070925 | A1 | 3/2015 | Berg-Hagen | |
| 2015/0369455 | A1* | 12/2015 | Nieminen | F21S 2/005 362/428 |

FOREIGN PATENT DOCUMENTS

| | | |
|---|---|---|
| JP | H01 134801 A | 5/1989 |
| JP | 2008262856 A | 10/2008 |
| JP | 2010/257742 A | 11/2010 |
| WO | 02/16824 A1 | 2/2002 |
| WO | 2008/093266 A1 | 8/2008 |
| WO | 2013-172718 | 11/2013 |

OTHER PUBLICATIONS

Finnish Search Report, dated Oct. 30, 2013, from corresponding FI application.

* cited by examiner

METHOD FOR CONTROLLING LIGHTING WITH A PORTABLE POINTER DEVICE

TECHNICAL FIELD

The application relates generally to a method for controlling lighting with a portable pointer device.

BACKGROUND

The hospital and dental operating rooms are required to have good lighting, particularly in those areas of operating rooms that are used for performing surgical operations. In addition, there is a need to focus lighting especially on those parts of a patient's body that are about to undergo surgical procedures.

U.S. Pat. No. 6,803,727 B2 discloses a lighting system, which is intended particularly for lighting an operating table. The system employs a pointer for focusing a lighting arrangement intended for lighting the operating table and mounted on the operating room ceiling.

The focusing is conducted by placing the pointer in the proximity of a body part on which the focusing of lighting is desired. The pointer's location is detected, for example optically, by detection instruments in communication with the lighting, whereby the location of an object of illumination, i.e. the pointer, is calculated-by-a-data-processing-unit-of-the-lighting and communicated thereby to an adjustment mechanism of the lighting arrangement made up by lighting modules, which focuses the lighting on the discussed site.

Alternatively, the focusing is conducted for example with a helmet fitted with a head-held infrared pointer in such a way that, when wishing to focus the lighting on a given site of the body, the surgeon aims the helmet's IR pointer thereat. A bright light spot visible at the indicated site is detected with an IR camera, whereby the data processing unit of lighting calculates, on the basis of information received from the IR camera, the location of an object ad communicates it to an adjustment mechanism for focusing the lighting on the desired site.

A problem with the foregoing focusing practices, when the desired object of illumination is located for example in the ear canal or in the mouth, is the directing of lighting in such a way that light is able to penetrate to the object as unimpededly as possible so as not to create distracting shadows on the object.

SUMMARY

It is one objective of the invention to eliminate the problems of available lighting systems and to concentrate the lighting of operating rooms so as to enable its focusing at an appropriate angle into a body cavity which is deep and possibly in a location unfavorable from the standpoint of lighting, whereby the creation of distracting shadows is as negligible as possible.

The one objective of the invention is attained with a method, a portable pointer device, and a lighting control system.

A method according to one embodiment, which is intended for controlling lighting with a portable pointer device, comprises determining, in the pointer device intended for the focusing of lighting, its position for establishing position data and transmitting the position data to a control unit intended for controlling a lighthead. The control unit controls the lighthead in such a way that the lighthead produces lighting for an object from a direction determined by the position data and location data, said location data having been established by determining a location of the pointer device in relation to the lighthead.

The term "lighting" is used in reference to the lighting of such facilities, in which is required effectively focusable lighting. The term refers for example to the lighting of operating rooms, dental offices, and other research and work facilities.

The term "portable pointer device" is used for example in reference to a handheld, effortlessly movable, and relatively lightweight pointer device which is cagable of communicating wirelessly by utilizing for example radio frequency (RF) or IR technology. The applied RF technology can be for example Bluetooth, Wibree, or WiFi.

The term "position" is used for example in reference to an orientation of the pointer device, i.e. in which direction the pointer device is aimed. The angle of inclination and the direction of inclination of a pointer device are determined in relation to the ground (floor of the facility) and/or to the lighthead, whose location is known by the control unit.

The pointer device according to one embodiment, which is intended for controlling lighting, has at least one processor and at least one memory comprising a computer program code. The at least one memory and computer program code are adapted, jointly with the at least one processor, to prompt the pointer device to at least determine a position of the pointer device intended for the focusing of lighting for establishing position data and to transmit the position data to a control unit intended for controlling a lighthead. The control unit controls the lighthead in such a way that the lighthead produces lighting for an object from a direction determined by the position data and location data, said location data having been established by determining a location of the portable pointer device in relation to the lighthead.

The computer program according to one embodiment, which is intended for controlling lighting with a portable pointer device and which computer program is executed with a processor, has a determination code for determining a position of the pointer device intended for the focusing of lighting and for establishing position data, and a transmission code for transmitting the position data to a control unit intended for controlling a lighthead. The control unit controls the lighthead in such a way that the lighthead produces lighting for an object from a direction determined by the position data and location data, said location data having been established by determining a location of the pointer device in relation to the lighthead.

The lighting control system according to one embodiment has a portable pointer device for focusing the lighting on an object, a lighthead for producing the lighting, a control unit for controlling the lighthead, and a detection unit for detecting a location of the pointer device in relation to the lighthead and for establishing location data. The pointer device includes at least one processor and at least one memory comprising a computer program code. The at least one memory and computer program code are adapted, jointly with the at least one processor, to prompt the pointer device to at least determine its position for establishing position data and to transmit the position data to a control unit. The control unit controls the lighthead in such a way that the latter produces lighting for an object from a direction determined by the position data and location data.

The invention according to the embodiments enables the work of an operating room physician to be facilitated as he/she no longer needs to wear any separate pointer device on his/her head, whereby no restrictions for the physician's movements are caused by a pointer device-equipped helmet.

The invention according to the embodiments enables also an effortless sterilization of a portable pointer device, improving at the same time the cleanliness of both the pointer device and the entire operating room or the like facility and forestalling the migration of impurities and disease carriers within the operating room and outside the operating room.

BRIEF DESCRIPTION OF THE FIGURES

Exemplary embodiments of the invention will be studied more precisely in a detailed description of the drawings with reference to the accompanying figures, in which.

DETAILED DESCRIPTION OF THE FIGURES

Figure 1:
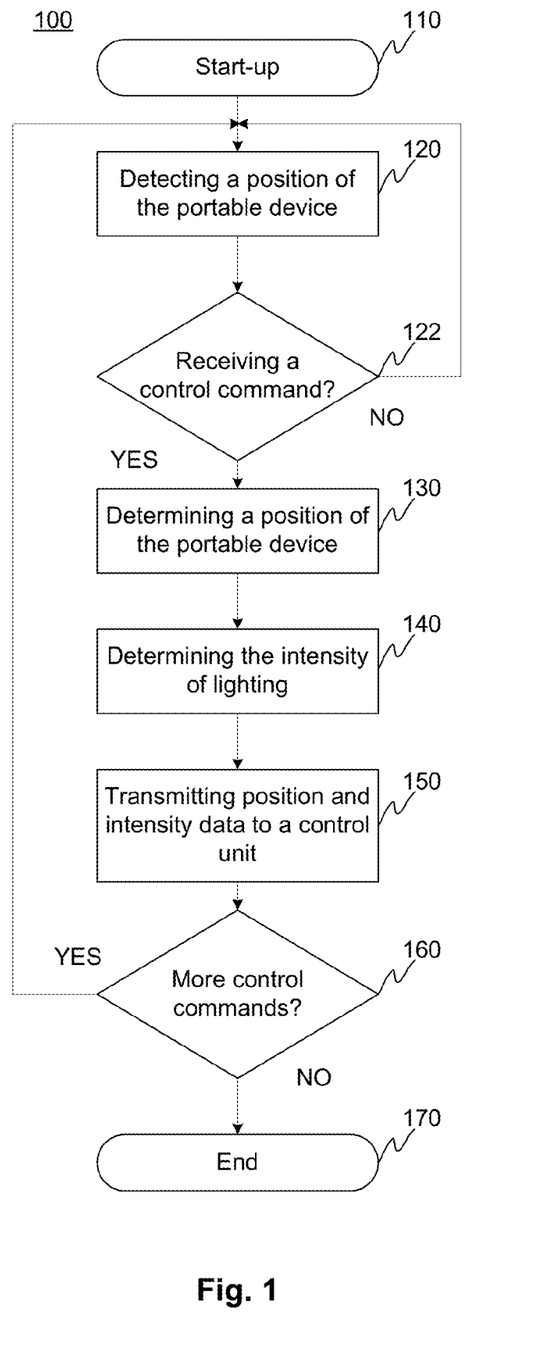
FIG. 1 shows a flowchart for a method carried out by a pointer device intended for controlling lighting.

FIG. 1 shows a method 100 for controlling the lighting of an operating room with a portable pointer device which is capable of communicating wirelessly with a lighting system control unit by using either RF and/or IR technology.

The lighting system comprises a lighthead for producing lighting, including at least one light element which in turn consists of at least one light emitting diode (LED), and the control unit enables, if necessary, each light element included in the lighthead to be controlled individually. By way of the control unit, it is possible to control light elements such that an object can be illuminated with at least one light beam which is generated by at least one light element. In the case of two or more light beams, each light beam is generated by at least one light element, and it is possible to adjust the properties of lighting produced by each light element so as to become different from each other one light beam at a time. The system further includes a detection unit whose function is to monitor a location of the pointer device in relation to the lighthead. The control unit is capable of communicating with several pointer devices simultaneously.

In a starting step 110, the system control unit and the pointer device are activated from their power switches, whereby, during the course of a starting sequence, both can update their sets of software, install new programs and/or delete old unnecessary programs and/or updates from the devices for maintaining the storage capacity thereof. If necessary, the control unit and the pointer device must be paired with each other. The patient, about to undergo an operation, is placed in an appropriate position on the operating table unless he/she is already in such a position. At the same time, the light elements of a lighthead are set to produce general lighting and the at least one light emitting diode of the pointer device is set to generate a light beam, by means of which the focusing of lighting on a correct site is managed more easily.

In step 120, at least one position sensor included in the pointer device begins to monitor a position of the pointer device, i.e. its orientation. The at least one position sensor comprises for example at least one acceleration sensor, which is adapted to obtain information regarding the angle of inclination and the direction of inclination of the pointer device, which constitutes position data of the pointer device when the pointer device is in the hand of its user and aimed in any given direction. The pointer device uses acceleration sensors along three axes for observing the orientation with respect to Earth's gravity and at the same time with respect to the lighthead. The pointer device can be fitted for example with three acceleration sensors suitable for measuring an angle of inclination and a direction of inclination.

A method 100 according to one embodiment, which is set forth in any of the preceding embodiments, comprises determining a position of the pointer device with at least one acceleration sensor.

When wishing to illuminate for example the palate of a patient, the user indicates with a pointer device towards the palate visible by way of the patient's open mouth, whereby the light emitting diode-generated light beam falls on the patient's palate, and pushes a control button of the pointer device, a so-called on/off button, whereby, in step 122, the pointer device receives a command for determining position data of the pointer device and produces by means of at least one acceleration sensor the position data of the pointer device in step 130.

In case a control command is not given in step 122, the pointer device continues observing its position in step 120.

In step 140, the intensity of lighting applied to the palate is determined in the pointer device and lighting intensity data is established. The determination of intensity is conducted for example with the same control button (on/off button) simultaneously with the generation of position data by determining the duration of pressing the control button. Alternatively, the adjustment may take place on the basis of a number of pushes applied to the control button. Optionally, for the adjustment of intensity there may also be a separate control button intended for its adjustment.

A method 100 according to one embodiment, which set forth in any of the preceding embodiments, comprises determining in the pointer device the intensity of lighting on the basis of a command, received by way of a control button intended for its adjustment, for establishing intensity data.

In step 150, the position data is transmitted wirelessly, for example by way of RF or IR communication, to a control unit intended for controlling a lighthead.

Having received the position data and the intensity data, the control unit obtains location data of the pointer device in relation to the lighthead from a detection unit. After receiving the location data, the lighthead controls, on the basis of the obtained data, the manipulation mechanisms operating the lighthead's light elements so as to enable application of lighting to the patient's palate in the direction of a body of the pointer device and of a light beam generated thereby, such that the lighthead produces lighting on the object exactly from a direction determined by the position data and the location data. The number of light elements used for lighting, and the intensity of lighting produced thereby, are determined on the basis of the received intensity data.

In the event that, in step 160, the user does not give a shutdown command to the pointer device, and the continued focusing of lighting is perhaps desired, the step 120 will be revisited.

On the other hand, if a shutdown command is received in step 160, the method comes to an end in step 170.

The pointer device can be equipped for example with a laser range finder or some other appropriate range finder with a capability of producing distance data which determines a distance between the pointer device and an object, i.e. in this case the palate. This particular data enables the control unit to be supplied with further information about the location of an object of illumination, thereby further enhancing the focusing of lighting and the adjustment of its intensity. The laser range finder or some other suchlike range finder is controlled by way of a specific separate button, a button intended for delivering the lighting command, or a combination of two buttons.

A method 100 according to one embodiment, which is set forth in any of the preceding embodiments, further comprises determining, in the pointer device, its distance to an object of illumination for establishing distance data.

The pointer device can also be outfitted for a capability of determining, in connection with a lighting command, the size and/or shape of an object of illumination. The user issues a command regarding an area of intended illumination to the pointer device by giving a control command and by indicating with a light beam the boundaries of the area of intended illumination. The indication may take place for example by drawing with the pointer device a circle or ellipse so as to cover an object of illumination, or by designating the area onto a patient's body by confining, for example by delimiting the area of intended illumination to the patient's open mouth. The user-issued control command is obtained by way of a separate button intended for the function, a button intended for giving the lighting command, or a combination of two buttons. The designated area is obtained from position data stored during the definition of boundaries, as well as from location data received from the detection unit.

A method 100 according to one embodiment, which is set forth in any of the preceding embodiments, further comprises determining, in the pointer device, the size and/or shape of an area of intended illumination on the basis of a command intended for the adjustment thereof and obtained by way of the control button, and on the basis of position data of the pointer device, for establishing area-related data.

The pointer device can also be outfitted for a capability of adjusting the color temperature of lighting produced by the light elements. The user issues an adjustment command and conducts the actual color temperature adjustment by way of separate button, a button intended for delivering the lighting command, or a combination of two buttons. The pointer device can also be of such a design that, instead of or in addition to color temperature, it is also possible to adjust at least one other optical property of lighting, such as for example intensifying and/or weakening the light of some specific spectral range with respect to the rest of the light, for example accentuating the color red or some other color as necessary.

A method 100 according to one embodiment, which is set forth in any of the preceding embodiments, further comprises determining the color temperature of lighting in the pointer device on the basis of a command, obtained by way of a control button intended for its adjustment, for establishing color temperature data.

A method 100 according to one embodiment, which is set forth in any of the preceding embodiments, comprises transmitting wirelessly, along with the position data, to the control unit at least one of the following: intensity data, distance data, and color temperature data, and the control unit controls the lighthead on the basis of data received thereby, including location data obtained from the detection unit.

Figure 2A:
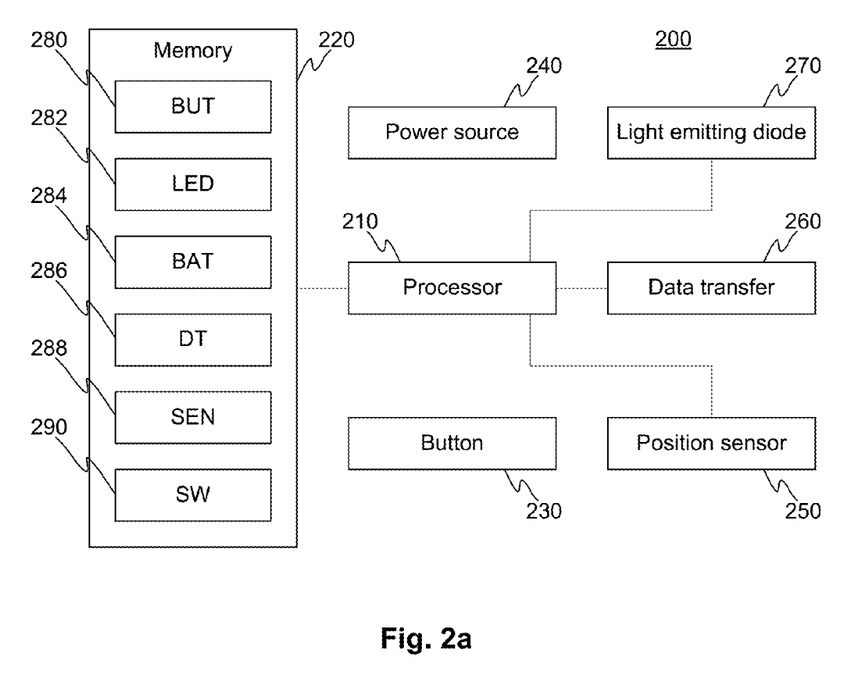
FIGS. 2a-2b show functional units for and the appearance of a pointer device carrying out the method.

FIG. 2a shows a portable pointer device 200 intended for controlling lighting, which has encapsulated therein at least one processor 210 which enables the execution of instructions determined for example by a user or an application program and the processing of data. The pointer device 200 has naturally at least one memory 220 for the storage and preservation of data, for example instructions, as well as at least one physical actuation button 230, for example an on/off button, as well as possibly one or more control buttons, for receiving the user's control commands. The at least one actuation button 230 may comprise separate actuation buttons for at least one of the following functions: the adjustment of lighting intensity, the control of a laser range finder (not shown), the determination of an area of intended illumination regarding its size/shape, and the adjustment of color temperature. The pointer device 200 may also be of such a design that, instead of or in addition to color temperature, it is also possible to adjust at least one other optical property of lighting, such as for example intensifying and/or weakening the light of some specific spectral range with respect to the rest of the light, for example accentuating the color red or some other color as necessary.

In addition, the pointer device 200 has at least one disposable or rechargeable battery 240 functioning as a power source, which is positioned in the pointer device 200 so as to enable its replacement or recharging by the use of a separate charger or a charging interface (not shown) included in the pointer device, at least one position sensor 250 for determining the orientation, a data transfer unit 260 comprising at least an RF and/or IR transmitter for communicating position data plus other data to the control unit in a wireless manner. The data transfer unit 260 may comprise optionally an RF and/or IR transceiver, whereby the pointer device 200 can have its software systems updated over a wireless communication from the control unit or some other computer. The pointer device 200 further includes a light emitting diode unit 270 comprising at least one light emitting diode for facilitating the focusing by means of a light beam generated thereby. The pointer device 200 may include also a second light emitting diode unit 270, comprising at least one light emitting diode, or a laser/IR transmitter, which is positioned at a second end of the elongated pointer device 200 and by means of which is determined one or more light elements used for illuminating an object.

The memory 220 comprises a program 280 controlling the operation of the at least one actuation button 230, a program 282 controlling the operation of the at least one light emitting diode 270, a program 284 controlling the operation of the at least one battery 240, a program 286 controlling the operation of the data transfer unit 260, a program 288 controlling the operation of the at least one position sensor 250, and a program 290 which enables a lighthead to be controlled by the pointer device 200.

In a portable pointer device 200 according to one embodiment, the computer program 290 stored in its memory 220 is adapted, jointly with the at least one processor 210, to prompt the pointer device 200 to determine a position of the pointer device 200, which is intended for the focusing of lighting, with at least one position sensor 250 for establishing position data, and to transmit, by means of the data transfer unit 260, the position data to a control unit, which is intended for controlling a lighthead and which controls the lighthead in such a way that the lighthead produces lighting an object from a direction determined by the position data and location data, said location data having been established by determining a location of the portable pointer device 200 in relation to the lighthead.

In a pointer device 200 according to one embodiment, which is set forth in any of the preceding embodiments, the pointer device 200 has its position determined by at least one acceleration sensor 250 and by at least one processor 210.

A pointer device 200 according to one embodiment, which is set forth in any of the preceding embodiments, is further adapted to determine, by means of at least one processor 210, the intensity of lighting on the basis of a command, obtained by way of a control button 230 intended for its adjustment, for establishing intensity data.

A pointer device 200 according to one embodiment, which is set forth in any of the preceding embodiments, is further adapted to determine, by means of at least one processor 210 and a laser range finder, its distance to an object of illumination for establishing distance data.

A pointer device 200 according to one embodiment, which is set forth in any of the preceding embodiments, is further adapted to determine, by means of at least one processor 210, the size and/or shape of an area of intended illumination on the basis of a command obtained by way of a control button 230 intended for the adjustment thereof, and on the basis of the position data of the pointer device 200, for establishing area-related data.

A pointer device 200 according to one embodiment, which is set forth in any of the preceding embodiments, is further adapted to determine, by means of at least one processor 210, the color temperature of lighting on the basis of a command, obtained by way of a control button 230 intended for its adjustment, for establishing color temperature data.

A pointer device 200 according to one embodiment, which is set forth in any of the preceding embodiments, is further adapted to transmit, by means of a data transfer unit 260, wirelessly along with the position data, to the control unit at least one of the following: intensity data, distance data, area-related data, and color temperature data, and the control unit controls a lighthead on the basis of data received thereby.

The computer program 290 according to one embodiment, which enables lighting to be controlled with a portable pointer device 200 and which is executed with a processor 210, has a determination code for determining a position and establishing position data of the pointer device 200 intended for the focusing of lighting, and a transmission code for transmitting the position data to a control unit, which is intended for controlling a lighthead and which controls the lighthead in such a way that the lighthead produces lighting for an object from a direction determined by the position data and location data, said location data having been established by determining a location of the pointer device 200 in relation to the lighthead.

A computer program 290 according to one embodiment, which is set forth in any of the preceding embodiments, further includes a determination code for determining the intensity of lighting and for establishing intensity data.

A computer program 290 according to one embodiment, which is set forth in any of the preceding embodiments, further includes a determination code for determining a distance to an object of illumination and for establishing distance data.

A computer program 290 according to one embodiment, which is set forth in any of the preceding embodiments, further includes a determination code for determining the size and/or shape of an area of intended illumination and for establishing area-related data.

A computer program 290 according to one embodiment, which is set forth in any of the preceding embodiments, further includes a determination code for determining the color temperature of lighting and for establishing color temperature data.

The computer program 290 can also be of such a design that, instead of or in addition to the color temperature, it is possible to adjust, by means of a determination code, at least one other optical property of lighting, such as for example intensifying and/or weakening the light of some specific spectral range with respect to the rest of the light, for example accentuating the color red or some other color as necessary.

A computer program 290 according to one embodiment, which is set forth in any of the preceding embodiments and which further includes a transmission code for transmitting position data wirelessly to a control unit along with at least one of the following: intensity data, distance data, area-related data, and color temperature data, said control unit controlling a lighthead on the basis of data received thereby.

In a computer program 290 according to one embodiment, which is set forth in any of the preceding embodiments, the discussed computer program is a computer program product, comprising a computer-readable data transfer medium provided with a computer program code intended to be executed by a computer.

Figure 2B:
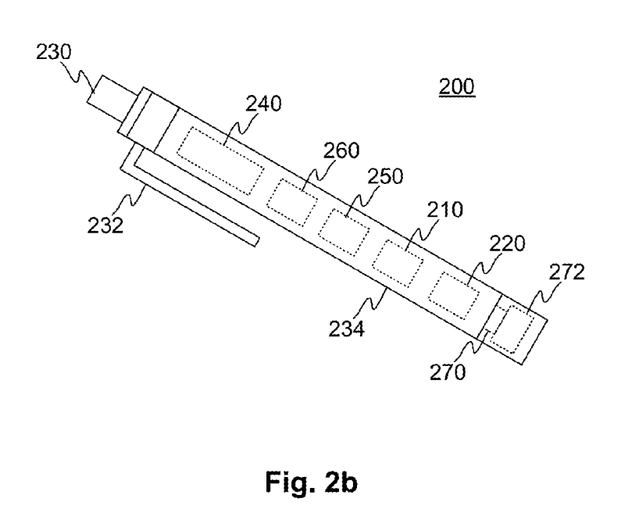

FIG. 2b shows the pointer device 200, a so-called light pen, inside whose cylindrical body 234 is packed the processor 210, the memory unit 220, the actuation button 230, by which is issued a lighting command by pushing it and the intensity of lighting is determined from the duration of a push, the replaceable battery 240, the position sensor unit 250, and the data transfer unit 260 equipped with an RF transmitter. A light beam intended for pointing is generated by the light emitting diodes 270 and optics 272 thereof. When not in use, the pointer device 200 can be suspended by a user from the edge of a pocket or the lapel of a jacket with a clip 232, under which is provided a threaded attachment (not shown) of the pointer device 200, whereby it can be opened for replacing the battery with a new one. The pointer device 200 may also come without the clip 232 for even easier cleaning of the pointer device 200. The pointer device 200 may also include a second light emitting diode, laser, or IR unit, which is placed at one end of the pointer device 200 to replace the actuation button 230. In this case, the actuation button 230 is fabricated along a side of the pointer device 200. It is possible to use this second unit for the determination of light elements used for the illumination of an object.

Figure 3:
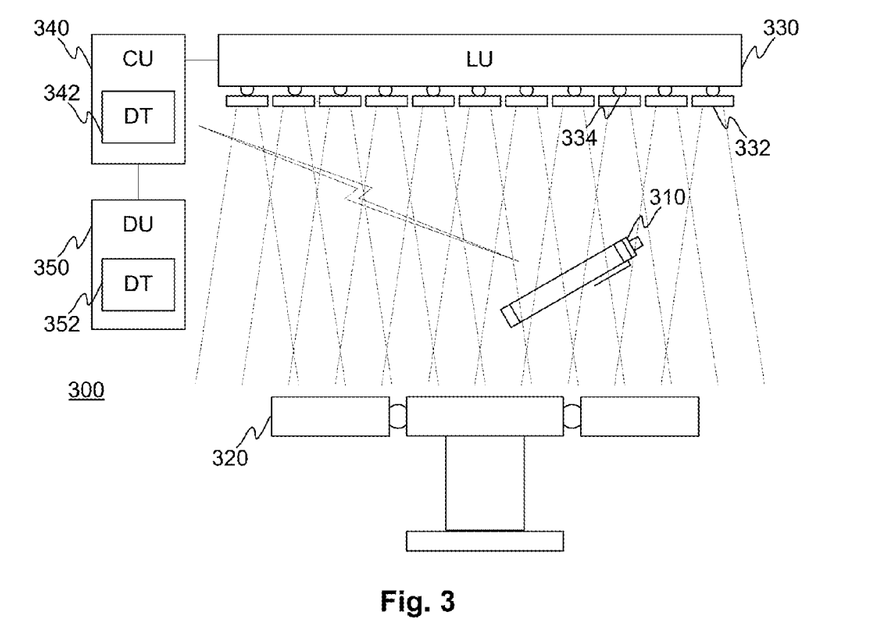
FIG. 3 shows a lighting control system.

FIG. 3 shows an operation room lighting control system 300, wherein a portable pointer device 310 is used for directing a lighthead 330, which is included in the lighting system and mounted on the ceiling of an operating room, and which comprises a plurality of light elements 332, each of which in turn consists of at least one light emitting diode and optics. The lighthead 330 additionally comprises just partly visible manipulation mechanisms 334, which are controlled by a control unit 340 of the system and by means of which it is possible to move the light elements 332 as a single entity, some of the light elements 332 as a group, or each light element 332 individually. With the pointer device 310, it is also possible to control the light elements 332 for example in such a way that an object can be illuminated with at least two or more discrete light beams, each of said light beams being generated by at least one light element 332. It is also possible for the properties of lighting produced by each light beam to be adjusted to differ from each other and each light beam to be pointed one at a time. The patient (not shown) about to undergo an operation is placed on an operating table 320, around and in the immediate vicinity of which the illumination produced by the lighthead 330 is possible to focus as desired. In FIG. 3, the light elements 332 are set to light the basic illumination directly downward without focusing.

The pointer device 310 has at least one processor, and at least one memory comprising a computer program, and the at least one memory and the computer program, jointly with the at least one processor, prompt the pointer device 310 at least to determine its orientation for establishing position data and to transmit wirelessly over an RF and/or IR communication the position data to the control unit 340 capable of controlling the lighthead 330 in such a way that it produces lighting for an object from a direction determined by the position data and location data of the pointer device 310.

The lighting control unit 340, which includes at least one processor, at least one memory, and at least one data transfer unit 342 comprising at least an RF and/or IR receiver, possibly also transmitter, by means of which it receives from the pointer device 310 the position data and possibly other information intended for controlling the lighting, for example lighting intensity information, distance information relating to the pointer device 310 and an object, information regarding the shape and/or size of an object of illumination, and lighting color temperature information, and/or information reflecting at least one other optical property of lighting, such as for example intensifying and/or weakening the light of some specific spectral range with respect to the rest of the light. The data transfer unit 342 enables transmission of commands and reception of information relating to a location of the pointer device 310 in a wireless manner for example over an RF and/or IR communication or, as shown in the figure, over a cable communication from a detection unit 350. The control unit 340 has stored in its at least one memory a computer program, which is adapted, on the basis of the received information, to determine a direction of illumination defined by the pointer device 310 as well as other parameters related to lighting, and to control, on the basis thereof, the operation of the lighthead's 330 light elements 332 and their manipulation mechanisms 334 in such a way that the focusing of lighting produced by the light elements 332 and desired by the user is successfully conducted in accordance with commands issued by the user with the pointer device 310. If necessary, the control unit 340 is capable of controlling individually every light element 332 included in the lighthead 330.

The system 300 further includes a detection unit 350, for example an IR camera or the like, whose function is to monitor a location of the pointer device 310 in relation to the lighthead 330 and, based on its observations, to establish location data which is used in the focusing of lighting. The detection unit 350 includes at least one processor, at least one memory, and at least one data transfer unit 352 comprising for example at least an RF and/or IR transmitter, possibly also receiver, by means of which it transmits the location data of the pointer device 310, detected thereby, either automatically or at the request of the control unit 340. Alternatively, the data transfer unit 352 can be adapted, as shown in the figure, to transfer data over a cable connection. The detection unit 350 has stored in its at least one memory a computer program, which is adapted to produce location data of the pointer device 310 and to transmit the same to the control unit 340.

In a control system 300 according to one embodiment, which is set forth in any of the preceding embodiments, the pointer device 310 has its position determined with at least one acceleration sensor.

In a control system 300 according to one embodiment, which is set forth in any of the preceding embodiments, the pointer device 310 therein is further adapted to determine the intensity of lighting on the basis of a command, obtained by way of a control button intended for its adjustment, for establishing intensity data.

In a control system 300 according to one embodiment, which is set forth in any of the preceding embodiments, the pointer device 310 therein is further adapted to determine its distance to an object of illumination for establishing distance data.

In a control system 300 according to one embodiment, which is set forth in any of the preceding embodiments, the pointer device 310 therein is further adapted to determine the size and/or shape of an area of intended illumination on the basis of a command obtained by way of a control button intended for the adjustment thereof, and on the basis of the position data of the pointer device 310, for establishing area-related data.

In a control system 300 according to one embodiment, which is set forth in any of the preceding embodiments, the pointer device 310 therein is further adapted to determine the color temperature of lighting on the basis of a command, obtained by way of a control button intended for its adjustment, for establishing color temperature data. The pointer device 310 can also be of such a design that, instead of or in addition to color temperature, it is possible to adjust at least one other optical property of lighting, such as for example intensifying and/or weakening the light of some specific spectral range with respect to the rest of the light.

In a control system 300 according to one embodiment, which is set forth in any of the preceding embodiments, the pointer device 310 therein is further adapted to transmit wirelessly, along with the position data, to the control unit 340 at least one of the following: intensity data, distance data, area-related data, and color temperature data, and/or some other data reflecting an optical property of lighting, and the control unit 340 controls the lighthead 330 on the basis of data received thereby, including location data received thereby from the detection unit 350.

Figure 4:
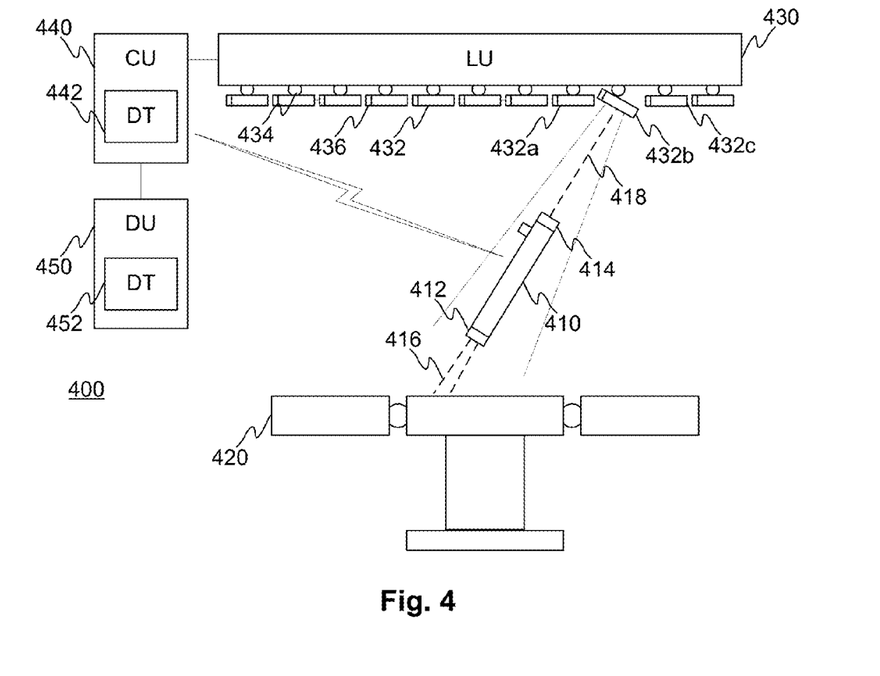
FIG. 4 shows an optional way of controlling light elements by means of the control system.

FIG. 4 shows a control system 400 similar to the previous figure, wherein the user operates a pointer device 410, which includes a light emitting diode unit 412 intended for pointing an object, and a light emitting diode, laser, or IR unit 414 set at the other end, for determining those light elements 432 of a lighthead 430 which participate in the illumination of an object, for example a patient. In the example of FIG. 3, on the other hand, the control center 340 determines, on the basis of previously agreed instructions and user-issued commands, those light elements 332, and the focusing thereof, which are to be used for lighting.

The lighthead 430 comprises a plurality of light elements 432, each having at least one light emitting diode and necessary optics as well as detection instruments 436, for example light sensors, which are adapted to detect an indication beam 418 co-directional with a body of the pointer device 410 and arriving from a unit 414. The detection instruments 436 can also be implemented in some other way, for example by mounting the same directly on a frame of the lighthead 430. In addition, the lighthead 430 includes just partially visible manipulation mechanisms 434, which are controlled by a control unit 440 and by means of which it is possible to move the light elements 432 the same way as described in connection with the previous figure.

The pointer device 410 only differs from that of the previous figure in the sense that it has an actuation button placed on a side of the pointer device 410 and it has a unit 414 for determining those light elements 432 of the lighthead 430 which participate in the lighting of an object.

The lighting control unit 440 and its data transfer unit 442 are similar to those presented in the previous figure, with the distinction that they are capable, jointly with the detection instruments 436, of determining the light elements 432 used for lighting. The detection unit 450 and its data transfer unit 452 are also functionally similar to those in FIG. 3.

When indicating an object (not shown) of illumination present on the operating table 420 with a light beam departing from the light emitting diode unit 412, the user activates the unit 414 from an actuation button located for example on a side of the pointer device 410 or from some other button, said unit generating a light beam 418 which is parallel to the object-pointing light beam 416 and the body of the pointer device 410. The detection instruments 436 identify the light element 432, towards or to the closest proximity of which light the light beam 418 falls in the lighthead 430, and communicate information about that to the control unit 440. On the basis of indication data of the light element 432, the position data and possibly other information intended for controlling the lighting, as well as the location data, received thereby as described in the previous example, the control unit 440 determines with how many light elements 432 and how the object will be illuminated. In the case of FIG. 4, the illumination is conducted with a light element 432b on which the light beam 418 falls, whereby the control unit 440 deflects, by means of manipulation mechanisms 434, the light element 432b in such a way that the illumination occurs co-directionally with the body of the pointer device 410. If necessary, the illumination can be enhanced for example by means of adjacent light elements 432a, 432c.

Respectively, the user can define with the pointer device 410 boundaries for an area of intended illumination, in which case the detection instruments 436 identify the light elements 432 on which the indicator beam 418 falls as the area boundaries are being defined. In the event that, when defining the area, the indicator beam 418 falls on light elements 432a, 432c, the illumination can be effected by using just those, or alternatively, by using all light elements 432a, 432b, 432c indicated by the indicator beam 418 and fallen inside the area defined thereby.

Described above are only a few exemplary embodiments of the invention. The principle according to the invention is naturally subject to modifications within the scope of protection defined by the claims, regarding for example implementation details and fields of use.

The invention claimed is:

1. A method for controlling lighting of an operating room with a portable pointer device, comprising:
   indicating, by the pointer device, a light element which is used for illuminating an object, to a control unit, the pointer device being configured for focusing of the lighting, the control unit being configured for controlling a light head, and the light head comprising a plurality of light elements;
   determining, in the pointer device a position for establishing position data, and
   transmitting by the pointing device the position data to the control unit, which controls the lighthead in such a way that the lighthead produces lighting, which is co-directional with a body of the pointer device, to the object by at least one light element by means of the position data and location data,
   wherein the pointer device and the control unit are separate entities,
   wherein the at least one light element comprises the indicated light element, and
   said location data having been established by determining a location of the pointer device in relation to the lighthead.

2. The method as set forth in claim 1, further comprising determining a position of the pointer device with at least one acceleration sensor.

3. The method as set forth in claim 1, further comprising determining, in the pointer device, the intensity of lighting on the basis of a command, obtained by way of a control button intended for its adjustment, for establishing intensity data.

4. The method as set forth in claim 1, further comprising determining, in the pointer device, its distance to the object of illumination for establishing distance data.

5. The method as set forth in claim 1, further comprising determining, in the pointer device, the size and/or shape of an area of intended illumination on the basis of a command obtained by way of a control button intended for the adjustment thereof, and on the basis of the position data of the pointer device, for establishing area-related data.

6. The method as set forth in claim 1, further comprising determining, in the pointer device, the color temperature of lighting on the basis of a command, obtained by way of a control button intended for its adjustment, for establishing color temperature data.

7. The method as set forth in claim 1, further comprising transmitting wirelessly, along with the position data, to the control unit at least one of the following: intensity data, distance data, and color temperature data, and the control unit controls the lighthead on the basis of data received thereby.

8. The method as set forth in claim 2, further comprising transmitting wirelessly, along with the position data, to a control unit at least one of the following: intensity data, distance data, and color temperature data, and the control unit controls the lighthead on the basis of data received thereby.

9. A computer program embodied in a non-transient storage medium, which is adapted to carry out a method as set forth in claim 1 when executed in a computer.

10. A lighting control system, which is adapted to carry out a method as set forth in claim 1.

11. The method as set forth in claim 2, further comprising determining, in the pointer device, the intensity of lighting on the basis of a command, obtained by way of a control button intended for adjustment, for establishing intensity data.

12. The method as set forth in claim 2, further comprising determining, in the pointer device, a distance of the pointing device to an object of illumination for establishing distance data.

13. The method as set forth in claim 2, further comprising determining, in the pointer device, a size and/or shape of an area of intended illumination on the basis of a command obtained by way of a control button configured for an adjustment thereof, and on the basis of the position data of the pointer device, for establishing area-related data.

14. The method as set forth in claim 2, further comprising determining, in the pointer device, a color temperature of lighting on the basis of a command, obtained by way of a control button intended for adjustment, for establishing color temperature data.

15. A portable pointer device for controlling lighting of an operating room, comprising:
at least one processor; and
at least one memory comprising a computer program embodied in a non-transient storage medium, wherein
the at least one memory and the computer program, together with the at least one processor, are adapted to cause the pointer device at least to indicate a light element, which is used for illuminating an object, to a control unit,
the pointer device is intended for a focusing of the lighting,
the control unit is intended for controlling a light head),
the light head comprises a plurality of light elements,
the pointer device is further configured to determine a position for establishing position data and to transmit the position data to the control unit, which controls the lighthead in such a way that the lighthead produces lighting, which is codirectional with a body of the pointer device, to the object by at least one light element) by means of the position data and location data,
the pointer device and the control unit are separate entities,
the at least one light element comprises the indicated light element, and
said location data having been established by determining a location of the pointer device in relation to the lighthead.

* * * * *